United States Patent [19]

Swenson

[11] Patent Number: 5,043,036

[45] Date of Patent: Aug. 27, 1991

[54] WIDTH STRETCHING DEVICE

[75] Inventor: Douglas A. Swenson, Maplewood, Minn.

[73] Assignee: Minnesota Mining and Manufacturing Company, St. Paul, Minn.

[21] Appl. No.: 502,328

[22] Filed: Mar. 30, 1990

[51] Int. Cl.⁵ .............................................. D06C 3/00
[52] U.S. Cl. ........................................ 156/160; 26/97; 26/99; 156/164; 156/495; 156/496; 156/498
[58] Field of Search ..................... 26/51, 97, 99, 88; 156/494, 495, 496, 164, 160, 161, 498

[56] References Cited

U.S. PATENT DOCUMENTS

| | | | |
|---|---|---|---|
| 2,582,165 | 1/1952 | Rosenfeld | 26/51 |
| 2,702,406 | 2/1955 | Reed | 26/51 |
| 3,639,917 | 2/1972 | Althouse | 2/DIG. 7 |
| 3,694,815 | 10/1972 | Burger | 2/237 |
| 4,227,952 | 10/1980 | Sabee | 156/204 |
| 4,523,969 | 6/1985 | Spencer | 156/161 |
| 4,626,305 | 12/1986 | Suzuki et al. | 156/164 |
| 4,642,150 | 2/1987 | Stemmler | 156/164 |
| 4,925,520 | 5/1990 | Beaudoin et al. | 156/164 |

Primary Examiner—David A. Simmons
Assistant Examiner—James J. Engel, Jr.
Attorney, Agent, or Firm—Gary L. Griswold; Walter N. Kirn; William L. Huebsch

[57] ABSTRACT

A device for stretching the width of strip material including two rotatably mounted circular pulleys having portions of their peripheries at a close spacing at a first location and portions of their peripheries at a larger spacing at a second location. Two flexible belts are mounted for movement along predetermined paths including clamping path portions with portions of the belts and pulleys in engagement from an inlet position adjacent the first location to an outlet position adjacent the second location. Edge portions of the strip material are guided between the belts and the peripheral surfaces at the inlet position and the portion of the strip material extending from the inlet position to the outlet position is clamped to the peripheral surface of the pulley by the belts and is stretched to widen its width as the pulleys rotate during movement of the strip material from the inlet position to the outlet position.

9 Claims, 3 Drawing Sheets

WIDTH STRETCHING DEVICE

TECHNICAL FIELD

The present invention relates to devices for progressively stretching elongate strip material between its edges to increase the width of the strip material.

BACKGROUND

U.S. Pat. application No. 438,593 filed Nov. 17, 1989, the content whereof is incorporated herein by reference, describes an elastomeric laminate comprising an elastomeric layer and at least one skin layer coextruded on one side of the elastomeric layer. An elongate strip of one embodiment of the elastomeric laminate (called a first embodiment herein) can be stretched across its width to up to 13 times its original width (and is typically stretched across its width in the range of 4 to 6 times its original width) at room temperature whereupon after the heat caused by such stretching is removed from the strip and tension on the strip is released, stresses in the skin layer of the elastomeric laminate will cause it to remain stretched until it is heated. After such heating the stresses induced by stretching in the skin layer of the elastomeric laminate will be relieved and the elastomeric laminate will shrink significantly and will subsequently be resiliently stretchable in (and only in) the direction it was stretched so that the elastomeric laminate can then serve as a resiliently elastic strip. An elongate strip of another embodiment of the elastomeric laminate (called a second embodiment herein) can be stretched across its width (typically in the range of 4 to 6 times its original width) at room temperature whereupon after the heat caused by such stretching is removed from the strip and tension on the strip is released, the elastomeric laminate will shrink significantly at room temperature and will subsequently be resiliently stretchable in (and only in) the direction it was stretched so that the elastomeric laminate can then also serve as a resiliently elastic strip. This second embodiment of the elastomeric laminate will remain stretched if cooled to a temperature significantly below room temperature (e.g., 0 degrees Fahrenheit) after widthwise stretching and before tension on the strip is released, and will subsequently shrink significantly at room temperature and attain its resiliently stretchable condition after again warming to room temperature.

While the elastomeric laminates described above are useful as elastic strips for many purposes, particularly including providing elastic strips in the waste bands of disposable garments or diapers, most existing production equipment is not suitable for applying the elastomeric laminates either because it does not include mechanisms that can stretch the strip material enough (i.e , stretching of the material in the range of 3 to 13 times its original width may be needed), or does not include mechanisms that can stretch the elastomeric laminate across its width, or does not include mechanisms that can remove heat caused by stretching the elastomeric laminate from the laminate.

DISCLOSURE OF INVENTION

The present invention provides a width stretching device that can either be used to pre stretch materials (including but not limited to elastomeric laminate materials of the types described above) across their widths so that existing stretching machinery incorporated in production equipment can complete stretching the material to the extent needed before the material is applied to an article such as a disposable diaper, or which device can be incorporated in a production line to stretch materials (including but not limited to elastomeric materials of the types described above) across their widths to the extent needed prior to application of cut lengths of the stretched material along a web or on articles.

According to the present invention there is provided a device for stretching elongate strip material having opposite edges and a predetermined width between its edges to increase the width of the strip material. The device comprises two circular pulleys mounted on a frame for rotation about their axes with the axes being oriented to position portions of the peripheral surfaces of the pulleys at a close spacing at a first location relative to the frame, and to position portions of the peripheral surfaces of the pulleys at a far spacing significantly greater than the close spacing at a second location relative to the frame and diametrically across the pulleys from the first location. Two continuous flexible belts are also provided. The belts and the pulleys have interacting guide means extending longitudinally along the belts and circumferentially around the peripheral surfaces of the pulleys for maintaining the belts in circumferential alignment around the peripheral surfaces of the pulleys. These interacting guide means are preferably provided by the peripheral surfaces of the pulleys having a plurality of spaced circumferentially extending ridges with recesses between the ridges, and the belts having along one side a plurality of longitudinally extending spaced ridges with recesses between the ridges; with the ridges on the belts being adapted to enter the grooves in the pulleys, and the ridges on the pulleys being adapted to enter the grooves in the belts. Means are provided mounting the belts on the frame for movement along predetermined paths including clamping path portions with the interacting guide means on the belts and pulleys in engagement from an inlet position adjacent the first location to an outlet position adjacent the second location with the belts being biased toward the pulleys. Edge portions of the strip material are guided between the belts and the peripheral surfaces at the inlet position and the strip material is guided away from the belts and the peripheral surfaces at the outlet position. The edge portions of the strip material extending from the inlet position to the outlet position will be clamped to the peripheral surfaces of the pulleys by the belts and the strip material will be stretched to widen its width between its edges as the pulleys rotate during movement of the strip material from the inlet position to the outlet position.

In such a device, the portions of the peripheral surfaces of the pulleys at the second location can be spaced a distance over 13 times greater than the distance between the portions of the peripheral surfaces of the pulleys at the first location to provide width stretching of the strip material, however, spacing the portions of the peripheral surfaces of the pulleys at the second location at a distance in the range of 4 to 6 times greater than the distance between the portions of the peripheral surfaces of the pulleys at the first location is more common for use with strips of the types of elastomeric laminate described above.

The diameter of the pulleys in such a device can be selected to regulate, within limits, the rate at which the strip material is stretched widthwise for any given rate of speed of the strip material through the device (i.e., large diameter pulleys causing a slower rate of stretching than relativelY small diameter pulleys).

The device can include means for driving the belts along their predetermined paths to move the strip material form the inlet position to the outlet position. The device can include means (e.g., a drum heated to 100 degrees Fahrenheit) at the inlet position to heat the strip material to a predetermined temperature and thereby facilitate stretching the strip across its width, and can provide means (e.g., a drum cooled to 30 degrees Fahrenheit) at the outlet position for cooling the strip material to remove heat generated by stretching from the strip material.

The device can be used to pre stretch material of the type described above so that existing stretching machinery incorporated in production equipment can complete stretching the material to the extent needed before the material is applied to an article such as a disposable diaper.

Alternatively, the device can be incorporated as stretching means in an assembly for applying in spaced relationship along a substrate lengths of a supply length of elongate strip material, which device comprises means defining a substrate path for guiding the substrate relative to a frame; means for moving the substrate at a first rate of speed along the substrate path; means defining a supply path relative to the frame and terminating at the substrate path for guiding the supply length of elongate strip material; means for moving the supply length of elongate strip material along the supply path at a second uniform rate of speed that is slower than the first rate of speed; the stretching means that sequentially stretches the supply length of the elongate strip material along the supply path to increase the width of the strip material; cutting means for cutting predetermined lengths from the supply length of elongate strip material between the stretching means and the substrate path; and means for applying the cut lengths of the elongate strip material in spaced relationship along the substrate.

That assembly can be used to apply a strip of the first embodiment of the elastomeric laminate described above that at room temperature remains stretched across its width so that it can be applied to a substrate in its stable stretched condition and can then be heated so that it will shrink across its width to about its original width while subsequently being resiliently stretchable in the direction it was stretched; or can be adapted to apply a strip of the second embodiment of the elastomeric laminate described above that after its initial stretching is resiliently stretchable across its width at normal room temperature, but can be retained in a stretched condition after being stretched across its width by cooling the strip material to a temperature substantially below room temperature. Such adaptation comprises providing means for cooling the strip material to a temperature substantially below room temperature and maintaining the strip material at that temperature after it is stretched and until it is applied to the substrate.

BRIEF DESCRIPTION OF DRAWING

The present invention will be further described with reference to the accompanying drawing wherein like reference numerals refer to like parts in the several views, and wherein.

DETAILED DESCRIPTION

Figure 1:
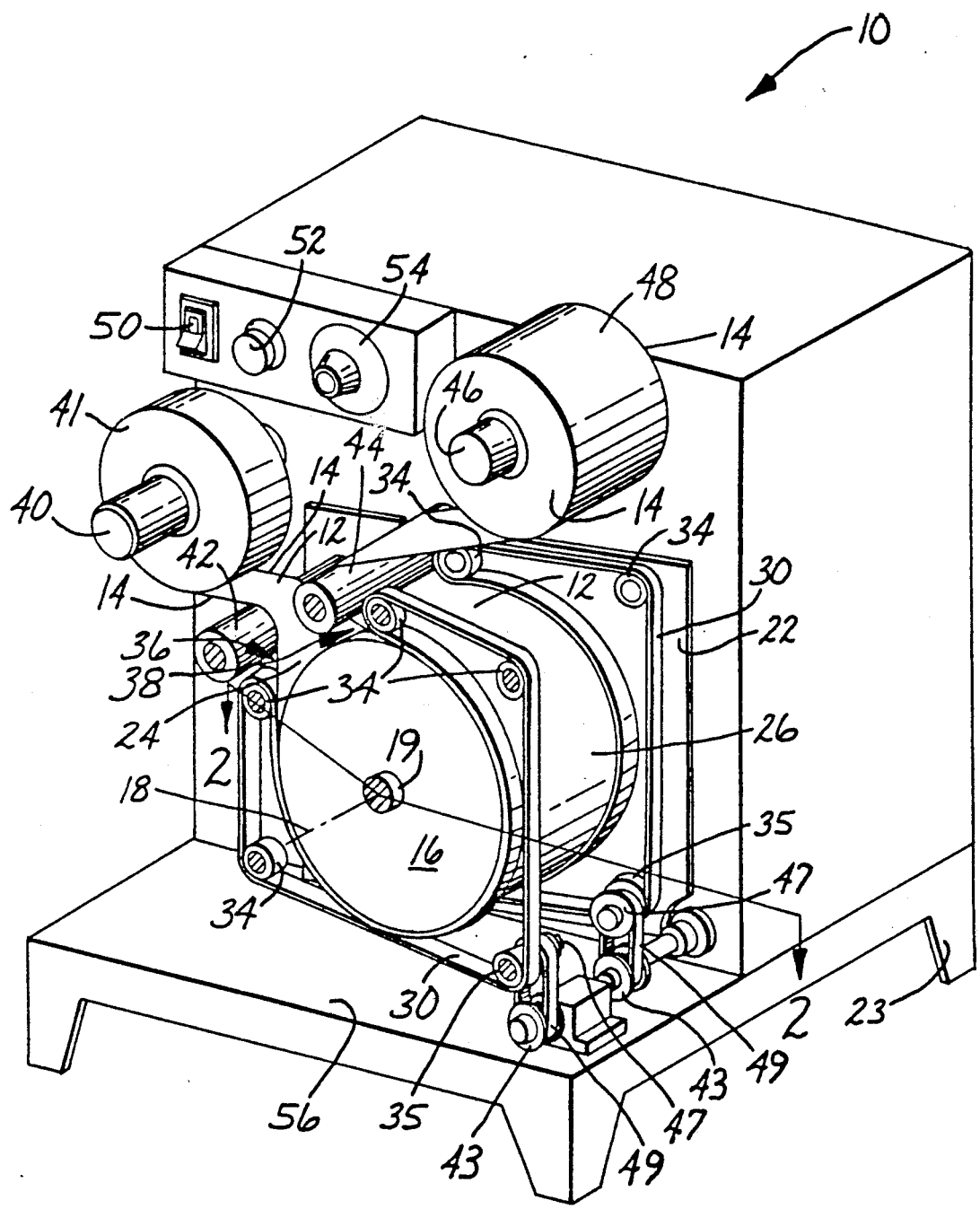
FIG. 1 is a perspective view of a first embodiment of a width stretching device according to the present invention having parts broken away to show detail.

Referring now to FIG. 1 of the drawing, there is shown a first embodiment of a width stretching device according to the present invention generally designated by the reference numeral 10.

Figure 2:
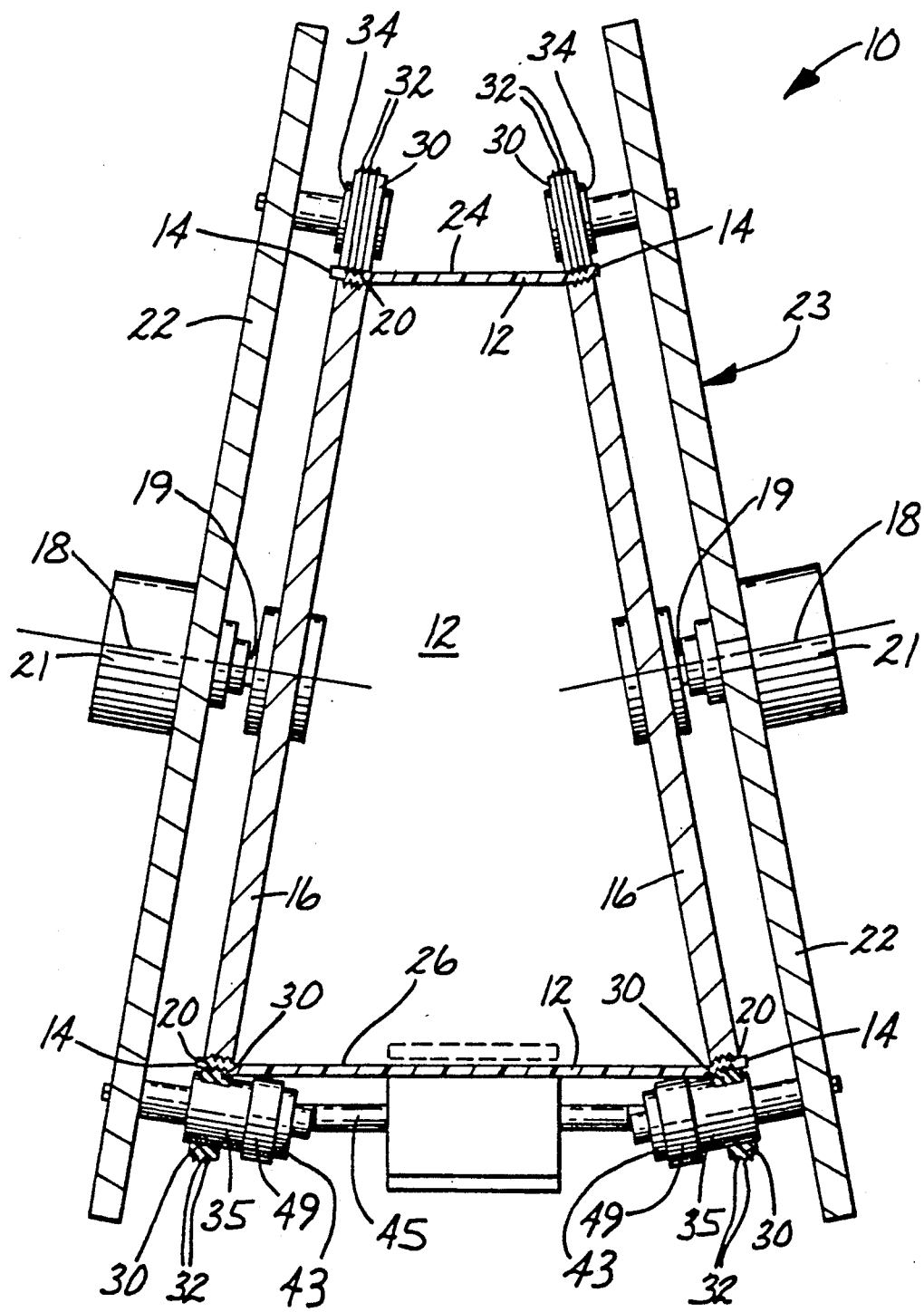
FIG. 2 is an enlarged fragmentary sectional view taken approximately along line 2—2 in FIG. 1.

Generally the width stretching device 10 is adapted for sequentially stretching elongate strip material 12 having opposite edges 14 and initially having a predetermined width between its edges 14 to increase the width of the strip material 12. The device 10 comprises two circular pulleys 16 of the same diameter each having an axis 18 and a peripheral surface around and disposed generally parallel to its axis 18, which peripheral surface is defined by a plurality of spaced ridges 20 with recesses between the ridges 20 (e.g., ridges 20 and recesses of the type provided on pulleys of the type in common use as the drive or driven pulleys on accessories for automobile engines and the like). Means in the form of shafts 19 fixed coaxially to the pulleys 16 and bearings 21 journalling those shafts 19 on plates 22 included in a frame 23 of the device 10 mount the pulleys 16 for rotation about their axes 18 with their axes 18 being oriented to position portions of the peripheral surfaces of the pulleys 16 at a close spacing at a first location 24 relative to the frame 22, and position portions of the peripheral surfaces of the pulleys 16 at a far spacing significantly greater than the close spacing at a second location 26 relative to the frame 22 and diametrically across the pulleys 16 from the first location 24 (e.g., the axes 18 being generally in the same plane and intersecting each other along that plane about midway between the pulleys 16 to define an obtuse included angle between the axes 18 as is shown in FIG. 2). The device 10 also includes two continuous flexible belts 30 having a plurality of spaced ridges 32 with recesses between the ridges 32 along one side (e.g., drive belts of the type commercially designated 770J4 that are available from Durkee-Atwood Company, Minneapolis, Minn.). The ridges 32 on the belts 30 are adapted to enter the grooves in the pulleys 16, and the ridges 20 on the pulleys 16 are adapted to engage the grooves in the belts 30. Means in the form of idler rollers 34 and a drive roller 35 rotatably mounted on the plates 22 included in the frame 23 are provided that mount the belts 30 for movement along predetermined paths including clamping path portions with the ridges 32 on the belts 30 along the grooves in the pulleys 16 and the ridges 20 on the pulleys 16 along the grooves in the belts 30 from an inlet position 36 adjacent the first location 24 to an outlet position 38 adjacent the second location 26 with the belts 30 being biased toward the pulleys 16 due to tension in the belts 30. Means provided by a hub 40 rotatably mounted on the frame 23 and supporting a supply roll 41 of the strip material 12 and an idler roller 42 also rotatably mounted on the frame 23 guide edge portions of the strip material 12 between the belts 30 and the peripheral surfaces of the pulleys 16 at the inlet position 36. Also, an idler roller 44 rotatably mounted on the frame 22 and a hub 46 supporting a take up roll 48 of the width stretched strip material 12 and rotatably mounted on the frame 23 by means that, through a slip clutch (not shown), apply a rotational torque to wind the strip material 12 onto the take up roll 48 provide means for guiding the strip material 12 away from the belts 30 and the peripheral surfaces of the pulleys 16 at the outlet position 38. The edge portions of the strip material 12 extending from the inlet position 36 to the outlet position 38 will be clamped to the peripheral surfaces of the pulleys 16 by the belts 30 and the strip material 12 will be stretched to widen its width between its edges 14 as the pulleys 16 rotate during movement of the strip material 12 from the first location 24 to the second location 26, after which, the strip material 12 can resiliently contract slightly across its width as the strip material 12 is carried from the second location 26 to the outlet position 38 which, while adjacent, are spaced from each other about 90 degrees around the peripheries of the pulleys 16 in the device 10 illustrated in FIGS. 1 and 2. Such spacing allows the strip material 12 to recover by about 50 percent of the maximum width to which it was stretched which is desirable for some types of strip material 12. Alternatively, the lengths of the belts 30 and the locations of the idler rollers 34 defining the outlet position 38 can be selected so that the outlet position 38 is closer to or at the first location 24 to retain more or all of the maximum width to which the strip material is stretched by the pulleys 16 and belts 30.

The device 10 may include means (not shown) for heating the roller 42 at the inlet position 36 (e.g., to a temperature of 100 degrees Fahrenheit) so that the roller 42 will heat the strip material 12 to a predetermined temperature and thereby facilitate stretching the strip material 12 across its width. The device 10 may also include means for cooling the roller 44 at the outlet position 38 (e.g., to a temperature of 30 degrees Fahrenheit) so that the roller 44 will cool the strip material 12 to remove heat generated by stretching from the strip material 12. Such heating and cooling of the rollers 42 and 44 facilitates rapid operation of the device 10, and when provided may require increasing the diameter of the rollers 42 and 44 and individually driving the rollers 42 and 44 to overcome their increased inertia caused by the heating and cooling apparatus.

The device 10 further includes drive means for driving the belts 30 along their predetermined paths to move the strip material 12 form the inlet position 36 to the outlet position 38. The drive means as illustrated includes two flanged drive pulleys 43 fixed to a shaft 45 driven through a gear reduction device (not shown) by a D.C. electric motor (also not shown), two drive pulleys 47 fixed coaxially to the two drive rollers 35, and two short timing drive belts 49 each around and in driving engagement between a different pair of the drive pulleys 43 and 47. The D.C. electric motor that drives the shaft 45 is controlled by control means including an on off switch 50, a jog switch 52 for momentarily actuating the motor as may be desirable, for example, during initial feeding of the strip, material 12 between the belts 30 and the pulleys 16, and a rotary knob 54 that controls the speed of the motor and thereby the speed of movement of the strip material 12 between the inlet and outlet positions 37 and 38.

As an example, the the pulleys 16 can have a diameter of about 30.5 centimeters (12 inches), the portions of the peripheral surfaces of the pulleys 16 at the second location 26 can be spaced by about 15.3 centimeters (6 inches), and the portions of the peripheral surfaces at the first location 24 can be spaced by about 2.9 centimeters (1.125 inches) which will stretch the portion of the strip material 12 between the pulleys 16 to about 4.8 times its original width between the first and second locations 24 and 26. The position of the vertically disposed plates 22 can also be adjustable within limits along a horizontal surface 56 of the frame 23 to change the spacing between the portions of the peripheral surfaces of the pulleys 16 at the second location 26 and/or the spacing between the portions of the peripheral surfaces at the first location 24 to thereby change the amount that the portion of the strip material 12 between the pulleys 16 will be stretched from its original width between the first and second locations 24 and 26.

Figure 3:
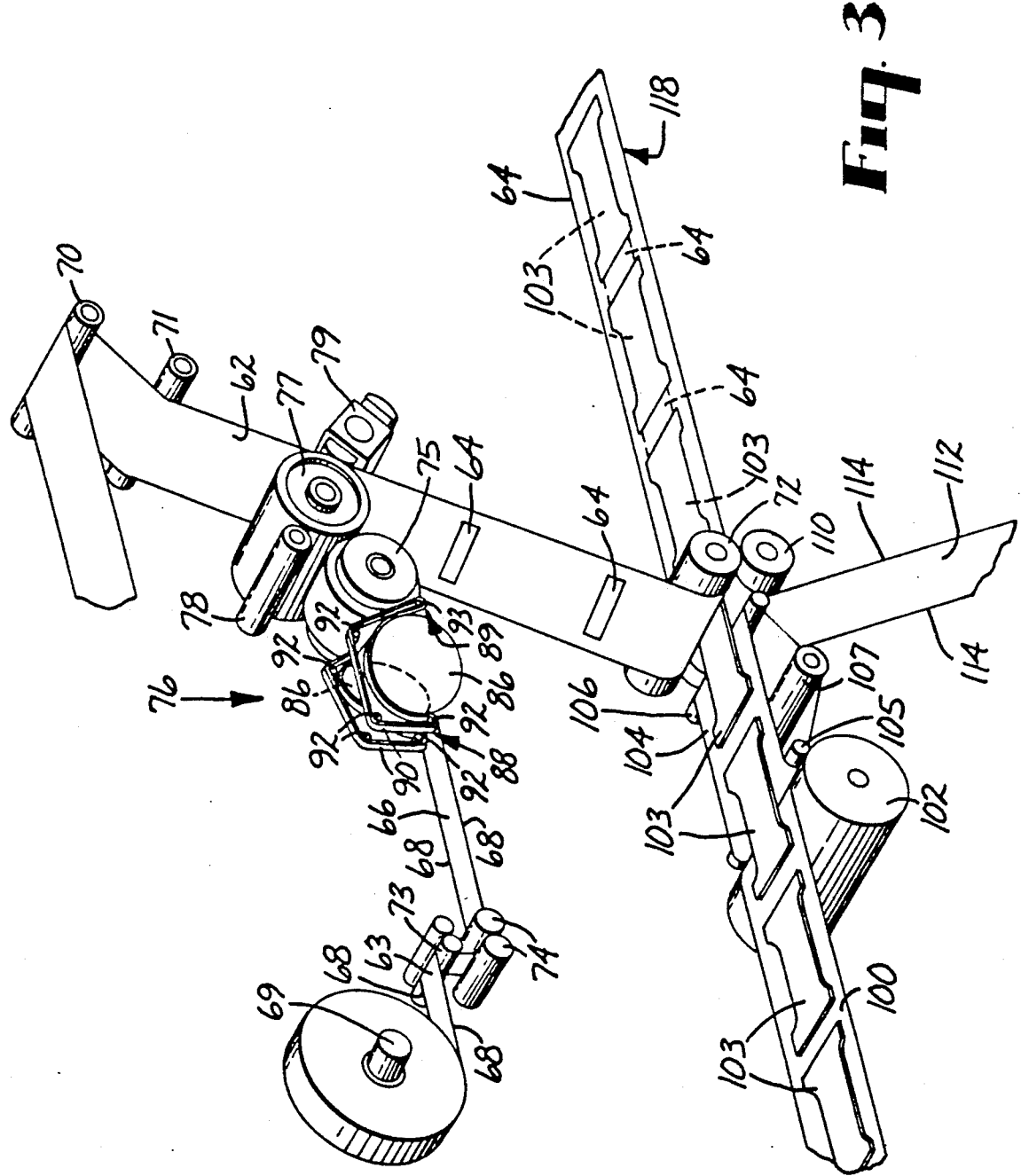
FIG. 3 is a schematic perspective view of an assembly for applying in spaced relationship along a substrate lengths of a supply length of elongate strip material that incorporates a second embodiment of a width stretching device according to the present invention.

Referring now FIG. 3 there is schematically illustrated an assembly 60 for applying in spaced relationship along a substrate 62 lengths 64 of a supply length 66 of elongate strip material having opposite edges 68 and a predetermined width between its edges 68. The assembly 60 comprises means including rotatably mounted guide rollers 70, 71 and 72 defining a substrate path for guiding the substrate 62 relative to a frame for the assembly (not shown); means (not shown) for moving the substrate 62 at a first rate of speed along the substrate path; means including a hub 69 rotatably supporting a supply roll of the strip material 12, rotatably mounted guide roller pairs 73 and 74, a cooling drum 75 and a vacuum drum 77 defining a supply path relative to the frame and terminating at the substrate path for guiding the supply length 66 of elongate strip material; means provided by a drive roller (not shown) pressed against the supply length 66 of elongate strip material along the cooling drum 75 for moving the supply length 66 of elongate strip material along the supply path at a second uniform rate of speed that is slower than the first rate of speed; stretching means 76 along the supply path for sequentially stretching the supply length 66 of the elongate strip material along the supply path to increase its width; cutting means including a rotary cutter 78 for cutting the predetermined lengths 64 from the supply length 66 of elongate strip material between the stretching means 76 and the substrate path; and applying means including the vacuum drum 77 and and a buffing roller 79 for applying the cut predetermined lengths 64 of the elongate strip material 66 in spaced relationship along the substrate 62.

The stretching means 76 is similar to the stretching device 10 described above in that it comprises two circular pulleys 86 each having an axis and a peripheral surface around its axis disposed generally parallel to its axis 88 and defined by a plurality of spaced ridges with recesses between the ridges; means (not shown but which could be plate like portions of the frame similar to the plates 22 of the device 10 parallel to and flanking the pulleys 86) mounting the pulleys 86 on the frame for rotation about their axes with the axes of the pulleys 86 being oriented to position portions of the peripheral surfaces of the pulleys 86 at a close spacing at a first location 88 relative to the frame, and position portions of the peripheral surfaces of the pulleys 86 at a far spacing significantly greater than the close spacing at a second location 89 relative to the frame and diametrically across the pulleys 86 from the first location 88; two continuous flexible belts 90 having a plurality of spaced ridges with recesses between the ridges along one side, the ridges on the belts 90 being adapted to enter the grooves in the pulleys 86, and the ridges on the pulleys 86 being adapted to engage the grooves in the belts 90; and means including idler rollers 92 and drive rollers 93 which are rotatably mounted on the frame (e.g., on the plate like portions of the frame flanking the pulleys 86) mounting the belts 90 on the frame for movement along predetermined paths including clamping path portions with the ridges on the belts 90 along the grooves in the pulleys 86 and the ridges on the pulleys 86 along the grooves in the belts 90 from an inlet position adjacent the first location 88 to an outlet position adjacent the second location 89 with the belts 90 being biased toward the pulleys 86 by tension in the belts 90; and means including the pair of guide rollers 74 for guiding edge portions of the strip material 66 between the belts 90 and the peripheral surfaces of the pulleys 86 at the inlet position and for guiding the stretched strip material 66 away from the belts 90 and the peripheral surfaces of the pulleys 86 at the outlet position so that the edge portions of the strip material 66 extending from the inlet position to the outlet position will be clamped to the peripheral surfaces of the pulleys 86 by the belts 90 and the strip material 66 will be stretched to widen its width between its edges 68 during rotation of the pulleys 86 and movement of the strip material 66 from the inlet position to the outlet position.

The assembly 60 may include means (not shown) for heating the pair of rollers 74 adjacent the inlet position (e.g., to a temperature of 100 degrees Fahrenheit) or may provide a heated drum (not shown) adjacent the inlet position so that the strip material 66 will be heated to a predetermined temperature at the inlet position to facilitate stretching the strip material 66 across its width. The cooling drum 75 may be cooled (e.g., to a temperature of 30 degrees Fahrenheit) to provide means at the outlet position for cooling the strip material 66 to remove heat generated by stretching from the strip material 66, which is useful when the assembly is used to apply the first embodiment of the elastomeric laminate described above.

The assembly 60 can be adapted to apply the second embodiment of the elastomeric laminate described above that once stretched is resiliently stretchable across its width at normal room temperature, but can be retained in a stretched condition after being stretched across its width by cooling the strip material 66 to a temperature substantially below room temperature. For such an adaptation means are provided on the assembly 60 for cooling the strip material 66 to a temperature substantially below room temperature and maintaining the strip material 66 at that temperature after the strip material 66 is stretched and until the strip material 66 is applied to the substrate 62, which means are provided by cooling the drum 75 and the vacuum drum 77 to a temperature substantially below room temperature (e.g., to 0 degrees Fahrenheit).

The assembly 60 in FIG. 3 is illustrated as a portion of an otherwise conventional production line for disposable diapers, which production line further includes a first conveyer belt 100 partially supported for movement by a roller 102 that conveys spaced absorbent diaper cores 103, a short accelerating conveyer comprising an endless belt 104 supported by three rollers 105, 106 and 107 which, with the substrate 62 can be run at a rate faster than the belt 100 to change the spacing between the diaper cores 103, a roller 110 around which is fed a length of polymeric film 112 (e.g., polypropylene) having lengths of elastic 114 adhered along its edges, and the roller 72 around which the substrate 62 with the lengths 64 of strip material adhered thereto are guided so that the film 112 and the substrate provide outer layers between which the diaper cores 103 are fed by the accelerating conveyer to provide a laminate from which individual diapers can be formed.

The present invention has now been described with reference to two embodiments thereof. It will be apparent to those skilled in the art that many changes can be made in the embodiments described without departing from the scope of the present invention. Thus the scope of the present invention should not be limited to the structures described in this application, but only by structures described by the language of the claims and the equivalents of those structures.

I claim:

1. An assembly for applying in spaced relationship along a substrate lengths of a supply length of elongate strip material having opposite edges and a predetermined width between said edges, said device comprising:

a frame;
   means defining a substrate path for guiding said substrate relative to said frame;
   means for moving said substrate at a first rate of speed along said substrate path;
   means defining a supply path relative to said frame and terminating at said substrate path for guiding said supply length of elongate strip material;
   means for moving said supply length of elongate strip material along said supply path at a second uniform rate of speed that is slower than said first rate of speed;
   stretching means along said supply path for sequentially stretching the supply length of the elongate strip material along the supply path to sequentially increase the width of the strip material;
   cutting means for cutting predetermined lengths from the supply length of elongate strip material between said stretching means and said substrate path; and
   means for applying said cut lengths of the elongate strip material in spaced relationship along said substrate, comprising:
      two circular pulleys each having an axis and a peripheral surface around said axis disposed generally parallel to said axis;
      means mounting said pulleys on said frame for rotation about said axes with said axes being oriented to position portions of the peripheral surfaces of the pulleys at a close spacing at a first location relative to the frame, and position portions of the peripheral surfaces of the pulleys at a far spacing significantly greater than said close spacing at a second location relative to the frame and diametrically across said pulleys from said first location;
      two continuous flexible belts;
      said belts and said pulleys having interacting guide means extending longitudinally along said belts and circumferentially around the peripheral surfaces of said pulleys for maintaining said belts in circumferential alignment around the peripheries of said pulleys;
      means mounting said belts on said frame for movement along predetermined paths including clamping path portions with said interacting guide means on said belts and pulleys in engagement from an inlet position adjacent said first location to an outlet position adjacent said second location with the belts being biased toward said pulleys; and means included in said means for defining said supply path for guiding edge portions of the strip material adjacent the edges of the strip material between said belts and said peripheral surfaces at said inlet position and for guiding said strip material away from said belts and said peripheral surfaces at said outlet position so that the edge portions of the strip material extending from said inlet position to said outlet position will be clamped to the peripheral surfaces of said pulleys by said belts and said strip material will be stretched to widen its width between its edges during rotation of said pulleys and movement of said strip material from said inlet position to said outlet position;

said means for guiding said strip material away from said belts and said peripheral surfaces at said outlet position including chilled roll means contacted by the stretched strip material for cooling the stretched strip material to retain the strip material in the stretched condition without the use of additional gripping means.

2. An assembly according to claim 1 wherein said interacting guide means along said belts and around the peripheral surfaces of said pulleys for maintaining said belts in circumferential alignment around the peripheries of said pulleys comprise the peripheral surfaces of said pulleys being defined by a plurality of spaced circumferentially extending ridges with recesses between said ridges, and said belts having along one side a plurality of longitudinally extending spaced ridges with recesses between said ridges, the ridges on said belts being adapted to enter the grooves in the pulleys, and said ridges on said pulleys being adapted to engage the grooves in said belts.

3. An assembly according to claim 1 particularly adapted to apply elongate strip material that is resiliently stretchable across its width at normal room temperature, but can be retained in a stretched condition after being stretched across its width by cooling the strip material to a temperature substantially below room temperature, wherein said chilled roll means contacted by the stretched strip material cools the strip material to a temperature substantially below room temperature and said assembly includes means for maintaining the strip material at that temperature after its is stretched and until it is applied to the substrate.

4. A device according to claim 1 wherein said axes of said pulleys are in generally the same plane and intersect each other along said plane about midway between said pulleys to define an obtuse included angle between said axes.

5. A device according to claim 1 further including mean driving said belts along said predetermined paths to move the strip material form said inlet position to said outlet position.

6. A device according to claim 1 wherein the portions of the peripheral surfaces of the pulleys at said second location are spaced a distance in the range of 3 to 13 times greater than the distance between the portions of the peripheral surfaces of the pulleys at said first location.

7. A device according to claim 1 wherein the pulleys have a diameter of about 30.5 centimeters (12 inches), the portions of the peripheral surfaces of the pulleys at said second location are spaced by about 15.3 centimeters (6 inches), and the portions of the peripheral surfaces at said first location are spaced by about 2.9 centimeters (1.125 inches).

8. A method for applying in spaced relationship along a substrate lengths of a supply length of elongate strip material having opposite edges and a predetermined width between its edges, which method comprises the steps of:

defining a substrate path for guiding the substrate;

moving the substrate at a first rate of speed along the substrate path;

defining a supply path terminating at the substrate path for guiding the supply length of elongate strip material;

moving the supply length of elongate strip material along the supply path at a second uniform rate of speed that is slower than the first rate of speed;

sequentially stretching the supply length of the elongate strip material along the supply path to sequentially increase the width of the strip material;

cutting predetermined lengths from the supply length of elongate strip material subsequent to said stretching step and before the substrate path; and applying the cut lengths of the elongate strip material in spaced relationship along the substrate, said stretching step comprising:

providing two circular pulleys each having an axis and a peripheral surface around its axis disposed generally parallel to its axis;

mounting the pulleys for rotation about their axes with their axes being oriented to position portions of the peripheral surfaces of the pulleys at a close spacing at a first location relative to the supply path, and position portions of the peripheral surfaces of the pulleys at a far spacing significantly greater than said close spacing at a second location relative to the supply path and diametrically across the pulleys from said first location;

providing two continuous flexible belts, the belts and the pulleys having interacting guide means extending longitudinally along the belts and circumferentially around the peripheral surfaces of the pulleys for maintaining the belts in circumferential alignment around the peripheries of the pulleys;

mounting the belts for movement along predetermined paths including clamping path portions with the interacting guide means on the belts and pulleys in engagement from an inlet position adjacent the first location to an outlet position adjacent the second location with the belts being biased toward the pulleys;

causing the means for defining the supply path to guiding edge portions of the strip material adjacent the edges of the strip material between the belts and the peripheral surfaces at said inlet position and to guide the strip material away from the belts and the peripheral surfaces at said outlet position so that the edge portions of the strip material extending from said inlet position to said outlet position will be clamped to the peripheral surfaces of the pulleys by the belts and the strip material will be stretched to widen its width between its edges during rotation of the pulleys and movement of the strip material from said inlet position to said outlet position; and cooling the strip material adjacent the outlet position by brining the stretched strip material into contact with the surface of a chilled toll to retain the strip material in the stretched condition without the use of additional gripping means.

9. A method according to claim 8 particularly adapted to apply elongate strip material that is resiliently stretchable across its width at normal room temperature, but can be retained in a stretched condition after being stretched across its width by cooling the strip material to a temperature substantially below room temperature, wherein said cooling step cools the strip material to a temperature substantially below room temperature and said method includes the further step of maintaining the strip material at that temperature after it is stretched and until it is applied to the substrate.

* * * * *